Aug. 6, 1957 E. S. BOERNER Plant Pat. 1,630
CHRYSANTHEMUM PLANT
Filed Dec. 5, 1956
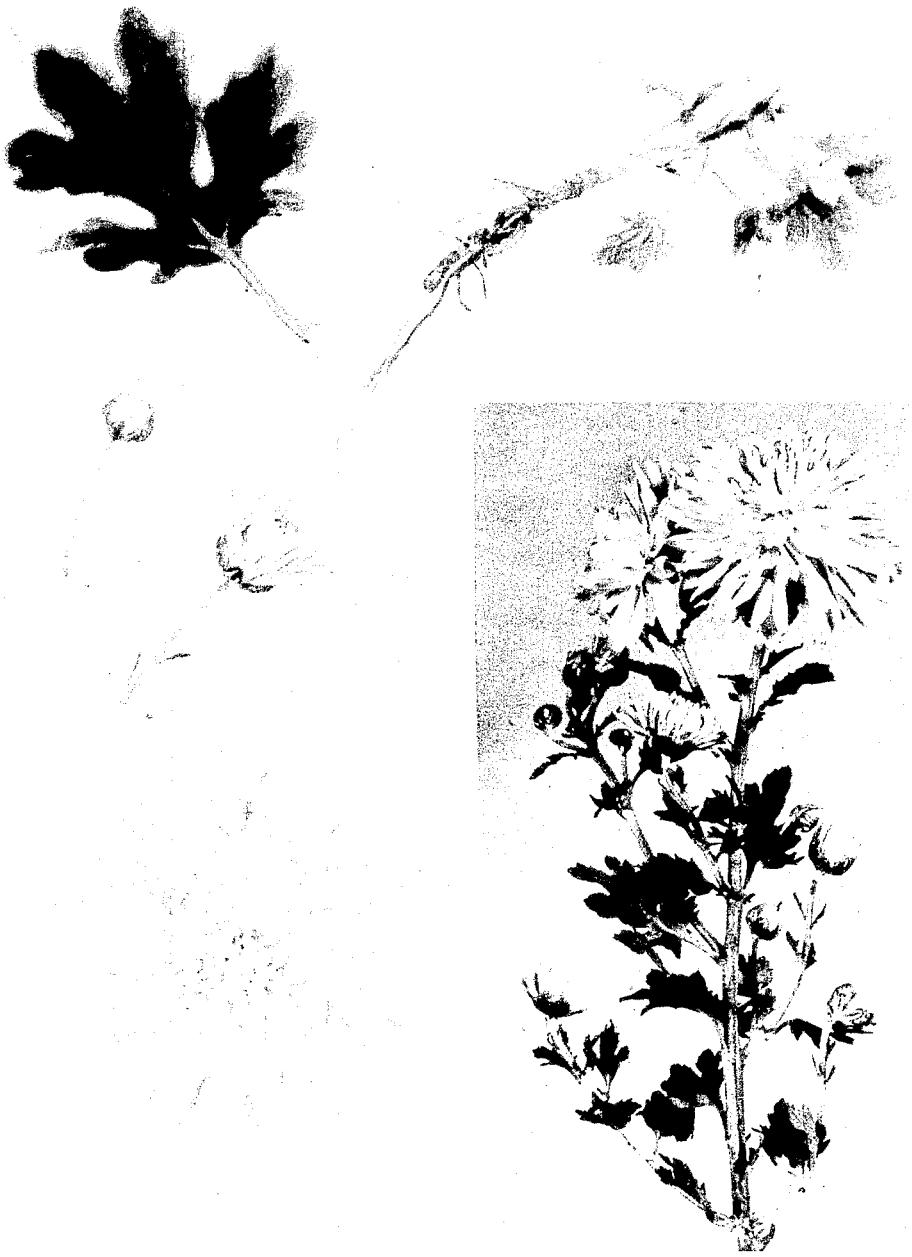
Inventor.
E. S. Boerner
By: Robbs & Robb
Attorneys.

United States Patent Office

Plant Pat. 1,630
Patented Aug. 6, 1957

1,630

CHRYSANTHEMUM PLANT

Eugene S. Boerner, Newark, N. Y., assignor to Jackson & Perkins Company, Newark, N. Y., a corporation of New York Application December 5, 1956, Serial No. 626,562

1 Claim. (Cl. 47—60)

The present invention relates to a new and distinct variety of chrysanthemum plant of the ball-type, which was originated by me by crossing the variety "Thrush" (Plant Patent No. 1,168) with the variety "Seagull" (Plant Patent No. 1,130).

The primary objective of this breeding was to produce a new chrysanthemum variety which bears flowers of a new distinctive color in the world of chrysanthemums. This objective was fully achieved, along with other improvements, as evidenced by the following characteristics which are outstanding in my new variety:

(1) Dark green silvery foliage;
(2) Large flowers of the ball-type;
(3) Pale Lilac, lightly overcast with Purplish Lilac, general color tonality of the flowers; and
(4) Long-lasting flowers.

The foregoing characteristics and distinctions definitely differentiate my new variety from its parents, as well as from all other varieties of its class of which I am aware, and asexual reproduction of the new variety by both top cuttings and underground runners, as performed at Newark, New York, shows that these characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character, and also shows a typical specimen plant in black-and-white which is illustrative of the form and habit of growth of the plant.

The following is a detailed description of my new variety, with color terminology in accordance with Ridgway's Color Standards and Nomenclature, as based upon observations made from specimens grown outdoors at Newark, New York, about mid-morning in the early part of October:

Parentage: "Thrush" × "Seagull."
Classification: Ball-type.

Growth: Very stiff; branching.
Cold resistance: Plants are winter-hardy in northern New York, and flowers are frost-resistant.
Blooming period: In the Newark, New York, climatic area, blooming usually begins about October 1st and continues until heavy freezes in October.

*Flower*

Bud:
*Color.*—When sepals first divide—Pale Vinaceous-Lilac, Plate 44. When petals begin to unfurl—Pale Vinaceous-Lilac, Plate 44, lightly overcast with Liseran Purple, Plate 26. When half-blown: inside of petals—Light Pinkish Lilac, Plate 37; reverse of petals—Light Pinkish Lilac, Plate 37, lightly overcast with Liseran Purple, Plate 26.
*Peduncle.*—Strong. Color—Kildare Green, Plate 31.
Bloom:
*Size.*—From 4 to 4½ inches.
*Stem.*—Stiff.
*Form.*—Ball-type.
*Petalage.*—Very double.
*Color.*—Center of flower—Pale Lilac, Plate 37, lightly overcast with Hay's Lilac, Plate 37. Outer petals—Pale Lilac, Plate 37. Inside of petals—Pale Lilac, Plate 37, lightly overcast with Purplish Lilac, Plate 37. Reverse of petals—White, Plate 53, lightly overcast with Pale Lilac, Plate 37.
*Petals.*—Texture—medium. Form—oval.
*Fragrance.*—Characteristic chrysanthemum.

*Plant*

Form: Upright; bushy.
Growth: Free.
Foliage:
*Size.*—Medium large.
*Quantity.*—Normal.
*Color.*—Upper side—Dark Cress Green, Plate 31, with a Silvery sheen. Reverse side—Light Elm Green, Plate 17.
*Texture.*—Leathery.

I claim:

A new and distinct variety of chrysanthemum plant of the ball-type flower, substantially as herein shown and described, characterized particularly as to novelty by its Dark Cress Green foliage and the silvery sheen thereof, the large size of its ball-type flowers, the distinctive Pale Lilac, lightly overcast with Purplish Lilac, general color tonality of its flowers, and the long-lasting quality of its flowers.

No references cited.